(12) United States Patent
Rollmann et al.

(10) Patent No.: US 8,532,941 B2
(45) Date of Patent: Sep. 10, 2013

(54) FATIGUE LIFE ESTIMATION METHOD AND SYSTEM

(75) Inventors: Georg Rollmann, Mülheim Ruhr (DE);
Marco Claudio Pio Brunelli, Orlando, FL (US)

(73) Assignee: Siemens Aktiengesellschaft, München (DE)

( * ) Notice: Subject to any disclaimer, the term of this patent is extended or adjusted under 35 U.S.C. 154(b) by 397 days.

(21) Appl. No.: 12/869,017

(22) Filed: Aug. 26, 2010

(65) Prior Publication Data
US 2012/0053858 A1    Mar. 1, 2012

(51) Int. Cl.
*G01L 5/00* (2006.01)
*G01L 25/00* (2006.01)
*G01B 5/00* (2006.01)

(52) U.S. Cl.
USPC ............................... 702/42; 702/34; 702/113

(58) Field of Classification Search
USPC ................................................ 702/34, 42, 113
See application file for complete search history.

(56) References Cited

U.S. PATENT DOCUMENTS

2009/0198470 A1* 8/2009 Lantieri et al. ............... 702/113
2011/0060568 A1* 3/2011 Goldfine et al. ............... 703/6

OTHER PUBLICATIONS

Johannesson, "Fatigue life prediction based on variable amplitude tests—methodology", 2005, International Journal of Fatigue, 954-965.*
Loren, "Estimating fatigue limit distributions under inhomogeneous stress conditions", 2004, International Journal of Fatigue, 1197-1205.*
Annovazzi-Lodi et al., "Statistical Analysis of Fiber Failures Under Bending-Stress Fatigue", Feb. 1997, Journal of Lightwave Technology, vol. 15, pp. 288-293.*
Pascual et al., "Analysis of Fatigue Data with Runouts Based on a Model with Nonconstant Standard Deviation and a Fatigue Limit", Jul. 9, 1996, pp. 1-25.*
Zheng et al., "Determination of Probablity Distribution of Fatigue Strength and Expressions of P-S-N. Curves", 1995, Engineering Fracture Mechanics, vol. 50, pp. 483-491.*

* cited by examiner

*Primary Examiner* — Marc Armand
*Assistant Examiner* — Ricky Ngon

(57) ABSTRACT

A method to estimate the fatigue life of a component operable under cyclic stress is provided. A system including testing device for performing a strain controlled test of a component or a representative specimen of the component, to obtain therefrom a first set of data samples including measured stress amplitude values for varying applied strain levels, and a second set of data samples including measured number of cycles to crack initiation for varying applied strain levels is also provided. The system further includes a modeling device for fitting a first low cycle fatigue material curve on the first set of data samples and a second low cycle fatigue material curve on the second set of data samples.

12 Claims, 3 Drawing Sheets

FATIGUE LIFE ESTIMATION METHOD AND SYSTEM

FIELD OF INVENTION

The present invention relates to a system and method for estimating fatigue life of components operating under cyclic stress, particularly, components subject to low-cycle fatigue (LCF).

BACKGROUND OF INVENTION

In a plurality of applications in technical systems parts or components can be subject to stresses which alternate or vary over time, of a mechanical or thermal nature for example. In such cases individual parts can for example be subject to direct mechanical stresses through the occurrence of compressive or tensile forces. A time-varying thermal stress of this type arises on the other hand for example for the parts or components in a turbine system, especially in a gas turbine, when the gas turbine is started up or shut down.

Extreme cyclic loading, both mechanical and thermal, results in material fatigue, also referred to as low cycle fatigue (LCF), which, in many cases limits the life of the component. The design of the components with respect to LCF life is done based on corresponding material curves which are determined in most cases by performing curve fits to experimental LCF test data. To avoid material failures during service life, a series of safety factors are taken into account while designing the component. These should, in particular, contain the uncertainties resulting from the determination of the material curves in estimating the fatigue life span of the component.

Now it is seen that the individual methods of fitting, for which a large number of degrees of freedom are available, differ vastly in teens of their robustness with respect to changes in the basic underlying measurement data. But since high uncertainties in the material curves would in turn lead to high uncertainties in estimated fatigue life spans, such a fit method that is not very robust would lead to high trade-offs in the calculated, allowable fatigue life spans, and hence indirectly to high costs.

A common way to determine LCF material curves is to use a simple approach based on linear regression and the principle of least squares (LS). However, as mentioned above, such a method is not optimal in terms of robustness. The uncertainties in the resulting material curves are taken as given and accounted for within the safety-factor concept.

SUMMARY OF INVENTION

The object of the present invention is to provide a method and system for robust and reliable determination of LCF material curves from experimental test data. These curves can then be used in order to estimate average LCF life times of components operating under cyclic loading.

The above object is achieved by the method according to the claims and the system according to the claims.

The underlying idea of the present invention is to customize or fit the LCF material curves to experimental data from strain controlled fatigue (LCF) tests in the framework of the statistical "Maximum Likelihood" theory. The (mid-life) stress amplitude as well as the number of cycles to crack initiation are considered as random variables. Depending on the underlying probability distribution functions as well as the curve parameters that are to be determined, the "curve fit" here changes into a problem of non-linear optimization that differs from a conventional least squares (LS) approach. The choice of stress amplitude and LCF life time as dependent variables (in contrast to, e.g., elastic, plastic, or total strain amplitudes) has proved to be beneficial with regard to the robustness of the method, which is thus more reliable and obviates the need for providing high factors of safety in fatigue life estimation.

Additional advantages are realized by embodiments according to the dependent claims.

In an exemplary embodiment, for improved reliability in obtaining LCF characteristics, said probability distribution functions $f_\sigma$ and $f_N$ represent log normal distributions.

In a preferred embodiment to aid computation, the computing of said first set and second set of curve parameters comprises determining those values of said parameters for which a negative logarithm of said likelihood functional 'L' assumes a minimum value, such that said likelihood functional 'L' is maximized.

In an exemplary embodiment, said first material curve (10) is defined by a Romberg-Osgood equation based relationship between stress '$\sigma_a$' and strain '$\epsilon_a$', wherein $$\varepsilon_a = RO(\sigma_a) = \frac{\sigma_a}{E} + \left(\frac{\sigma_a}{K'}\right)^{1/n'},$$

and wherein E, K' and n' form said first set of parameters $\theta_{C1}$ whose values are determined such that said likelihood functional 'L' is maximized.

In an exemplary embodiment, said second LCF material curve (20) is defined by a Coffin-Manson-Basquin equation based relationship between strain '$\epsilon_a$' and number of cycles to crack initiation wherein $$\varepsilon_a = CMB(N_i) = \frac{\sigma'_f}{E}(2N_i)^b + \varepsilon'_f(2N_i)^c,$$

and wherein $\epsilon'_f$, $\sigma'_f$, E, b and c form said second set of parameters $\theta_{C2}$ whose values are determined such that said likelihood functional 'L' is maximized.

In one embodiment, at least one of said parameters in said first and second set of parameters has predetermined fixed value from known material characteristics of said component (6). By fixing the value of one or more parameters, for example, by incorporating prior knowledge of material properties, the computational burden on the system may be reduced.

In accordance with another aspect of the present invention, a method is provided for operating a component under cyclic stress, said method comprising scheduling a downtime or maintenance interval of said component taking into account an estimated fatigue life of said component, said estimated fatigue life being determined by a method according to any of the above-mentioned embodiments.

In an exemplary embodiment, said component is a gas turbine component. The present invention is particularly useful for gas turbine components which operate under high cyclic stress (both mechanical and thermal) and hence prone to low cycle fatigue.

BRIEF DESCRIPTION OF THE DRAWINGS

The present invention is further described hereinafter with reference to illustrated embodiments shown in the accompanying drawings, in which.

DETAILED DESCRIPTION OF INVENTION

Figure 1:
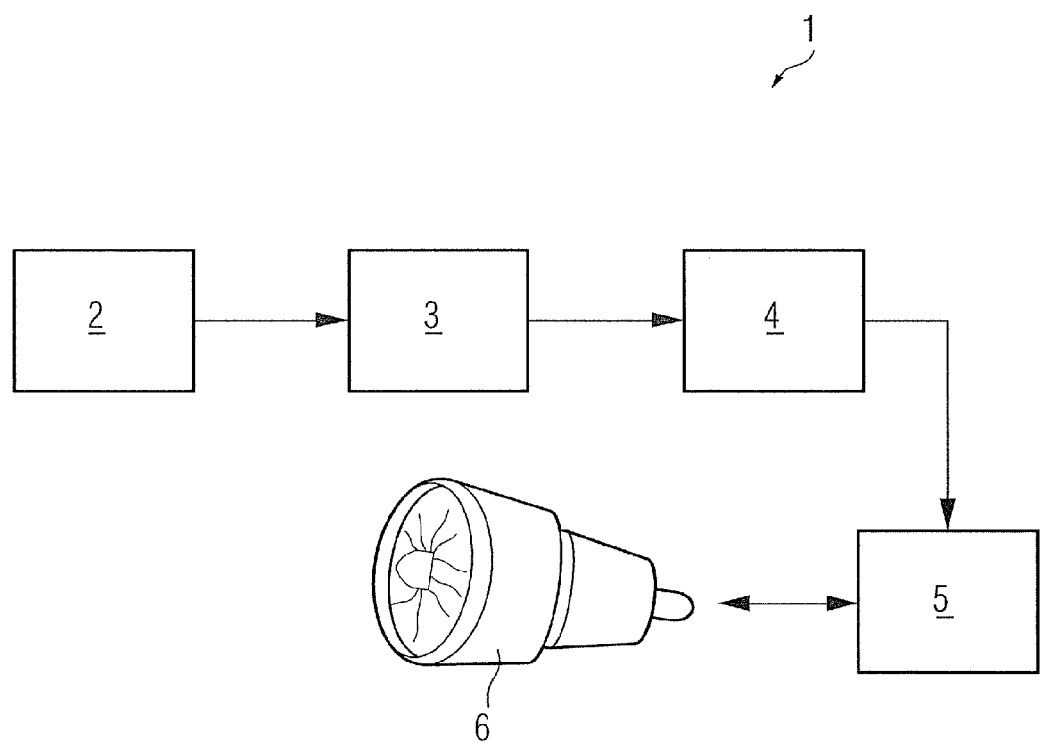
FIG. 1 a system for managing operation of a component subject to cyclic stress based on fatigue life estimation.

Referring no to FIG. 1 is illustrated an exemplary system 1 for operating a component 6 based on fatigue life estimation of the component 6. An important aspect of the fatigue process is plastic deformation. Fatigue cracks usually nucleate from plastic straining in localized regions. Therefore cyclic strain-controlled tests have been found to better characterize fatigue behavior of the component than cyclic stress-controlled tests, particularly in the low cycle fatigue (LCF) region. To that end, the illustrated system 1 broadly includes testing means 2 for obtaining strain-controlled LCF test data of the component 6 or a specimen representative of the component 6, modeling means 3 for fitting LCF material curves on the data samples obtained from the testing means 2, design means 4 for determining an estimated fatigue life of the component 6 on the basis of these LCF material curves, and control means 5 for controlling downtime or maintenance interval of the component 6 taking into account the estimated fatigue life of the component 6. In the illustrated embodiment, the component 6 is a gas turbine component. However, the present invention may be applied for any component undergoing high cyclic stresses, including mechanical and/or thermal stresses.

The testing means 2 may comprise, for example, a servo-controlled closed loop testing machine, a portion (length) of component 6 or the representative specimen having a uniform gage section is subject to axial straining. An extensometer may be attached to the uniform gage length to control and measure the strain over the gauge section. In the illustrated embodiment, a first strain-controlled test performed on the component/specimen involves applying a completely reversed cyclic straining to the component/specimen and measuring the corresponding stress amplitudes for various test strain (amplitude) levels. A second strain-controlled test performed on the component/specimen involves, for different test strain (amplitude) levels, applying a completely reversed cyclic straining on the component/specimen with constant strain amplitude till fatigue failure (i.e., crack initiation) of the component/specimen occurs, and measuring the number of cycles to crack initiation for each test strain (amplitude) level.

Figure 2:
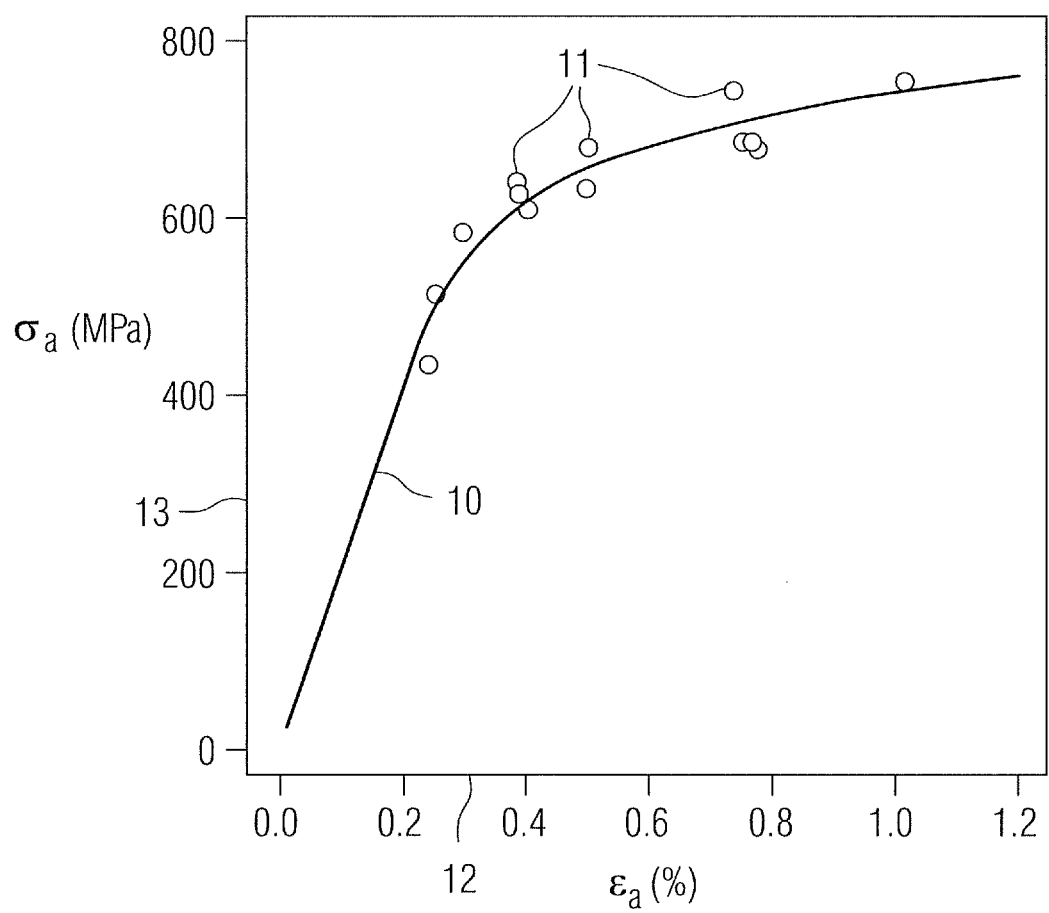
FIG. 2 is a graphical representation showing a stress-strain curve fitted on a set of data samples comprising measured stress amplitude values for varying applied strain levels.
Figure 3:
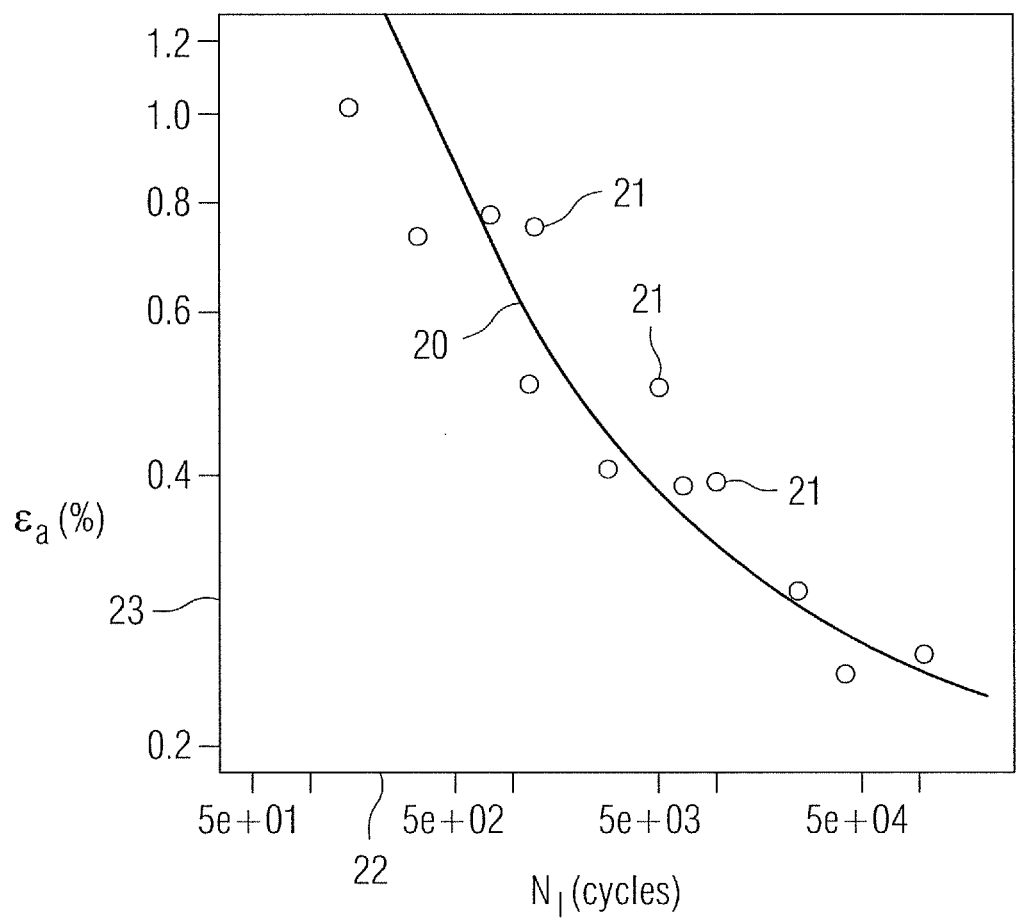
FIG. 3 is a graphical representation showing a strain-life curve fitted on a set of data samples comprising measured number of cycles to crack initiation for varying applied strain levels.

As shown in FIG. 2, from the first strain-controlled test, a first set of data samples 11 may be obtained plotting measured stress amplitude $\sigma_a$ (represented along the axis 12) against test strain level $\epsilon_a$ (represented along the axis 13). As shown in FIG. 3, from the second first strain-controlled test, a second set of data samples 21 may be obtained plotting measured cycles to crack initiation $N_i$ (represented along the axis 22) against test strain level $\epsilon_a$ (represented along the axis 23).

Referring back to FIG. 1, based on the data samples obtained from the strain-controlled tests, the modeling means 3 generates LCF stress-strain and strain-life curves for the component/specimen. The underlying idea herein is to fit the LCF material curves to the data samples obtained from the strain-controlled tests in the light of the statistical "Maximum Likelihood" theory, wherein the amplitude of the stress and the number of cycles to incipient fatigue cracking are considered as random variables. The modeling means 3, which forms an essential feature of the present invention, includes a computing device such as a PC or a general purposed microprocessor having suitable hardware for implementing the computational steps described below.

The first LCF material curve, namely, stress-strain curve to be fitted on the first set of data samples, is defined by a first set of curve parameters, while the second curve, namely, strain-life curve to be fitted on the second set of data samples, is defined by a first set of curve parameters. The objective of the proposed "curve "fit" method is to numerically determine the values of the above-mentioned curve parameters for which a likelihood function 'L' as defined in equation (1) is maximized.

$$L := \prod_{j=1}^{n} f_\sigma(\sigma_{a,j} \mid \theta_{C1}, \varepsilon_{a,j}) \cdot \prod_{k=1}^{m} f_N(N_{i,k} \mid \theta_{C2}, \varepsilon_{a,k}) \quad (1)$$

where
$f_\sigma$ and $f_N$ are probability distribution functions,
$\epsilon_{a,j}$ and $\epsilon_{a,k}$ represent test strain levels in the first and second sets of data samples respectively,
$\sigma_{a,j}$ represents measured stress amplitude values in the first set of data samples
$N_{i,k}$ represents the measured number of cycles to crack initiation in the second set of data samples, and
$\theta_{C1}$ and $\theta_{C2}$ represent the first set and second set of curve parameters respectively whose values have to be determined such that the likelihood functional 'L' is maximized.

Depending on the probability distribution functions used as well as the curve parameters that are to be determined, the "curve fit" here changes into a problem of non-linear optimization that differs from a conventional least squares (LS) fit method. In the embodiment illustrated herein, the probability distribution functions $f_\sigma$ and $f_N$ represent log normal distribution. However, alternate embodiments may incorporate other types of probability distribution, such as Weibull distribution. As illustrated below, the computation involved herein comprises determining values of the sets of parameters $\theta_{C1}$ and $\theta_{C2}$ for which a negative logarithm of the likelihood functional 'L' is minimized.

As an example, the first LCF material curve may defined by a Romberg-Osgood equation based relationship between stress '$\sigma_a$' and strains '$\epsilon_a$' as expressed in equation (2) below:

$$\varepsilon_a = RO(\sigma_a) = \frac{\sigma_a}{E} + \left(\frac{\sigma_a}{K'}\right)^{1/n'} \quad (2)$$

wherein E, K' and n' form the first set of parameters $\theta_{C1}$, referred to subsequently herein as Romberg-Osgood parameters, or $\theta_{RO}$.

Again, as an example, the second LCF material curve may be defined by a Coffin-Manson-Basquin equation based relationship between strain '$\epsilon_a$' and number of cycles to crack initiation '$N_i$' as expressed in equation (3) below:

$$\varepsilon_a = CMB(N_i) = \frac{\sigma'_f}{E}(2N_i)^b + \varepsilon'_f(2N_i)^c \quad (3)$$

wherein $\epsilon'_f$, $\sigma'_f$, E, b and c form the second set of parameters $\theta_{C2}$, referred to subsequently herein as Coffin-Manson-Basquin parameters, or $\theta_{CMB}$.

Thus, in this example, the problem involves determining $\theta_{RO}$ and $\theta_{CMB}$ such that the negative logarithm of the likelihood functional 'L' is minimized. As mentioned above, the probability distribution functions $f_\sigma$ and $f_N$ in this case represent log normal distributions. For the probability distribution functions $f_\sigma$ and $f_N$, the corresponding median values for $\sigma_a$ and $N_i$ are given respectively by equations (2) and equations (3) mentioned above. That is to say the median value for $\sigma_a$ is $RO^{-1}(\epsilon_{a,j}|\theta_{RO})$ and the median value of $N_i$ is $CMB^{-1}(\epsilon_{a,k}|\theta_{CMB})$. The variances for log $\sigma_a$ and log $N_i$ are assumed to depend on $\epsilon_a$. Based on the above considerations, the problem may be considered to be that of minimizing the expression given by equation (4):

$$-\log L := \sum_{j=1}^{n} \log\sqrt{2\pi\sigma_{RO}^2(\varepsilon_{a,j})} + \qquad (4)$$

$$\frac{1}{2\sigma_{RO}^2(\varepsilon_{a,j})} \cdot (\log\sigma_{a,j} - \log RO^{-1}(\varepsilon_{a,j} \mid \theta_{RO}))^2 +$$

$$\sum_{k=1}^{m} \log\sqrt{2\pi\sigma_{CMB}^2(\varepsilon_{a,k})} +$$

$$\frac{1}{2\sigma_{CMB}^2(\varepsilon_{a,k})} \cdot (\log N_{i,k} - \log CMB^{-1}(\varepsilon_{a,k} \mid \theta_{CMB}))^2$$

As shown to one skilled in the art, the parameters in $\theta_{RO}$ and $\theta_{CMB}$ may be constrained to fulfill equations (5a) and (5b) below:

$$\sigma'_f = K' \cdot (\epsilon'_f)^{n'} \qquad (5a)$$

$$b = n' \cdot c \qquad (5b)$$

Based on the interrelation mentioned above, and assuming that the variances $\sigma_{RO}$ and $\sigma_{CMB}$ are constant, the problem may be finally considered to be reduced to minimizing the expression given by equation (6)

$$-\log L := \sum_{j=1}^{n} \log\sqrt{2\pi\sigma_{RO}^2} + \qquad (6)$$

$$\frac{1}{2\sigma_{RO}^2} \cdot (\log\sigma_{a,j} - \log RO^{-1}(\varepsilon_{a,j}, E, K', n'))^2 + \sum_{k=1}^{m} \log\sqrt{2\pi\sigma_{CMB}^2} +$$

$$\frac{1}{2\sigma_{CMB}^2} \cdot (\log N_{i,k} - \log CMB^{-1}(\varepsilon_{a,k}, E, K', n', \sigma'_f, b))^2.$$

The above non-linear functional is minimized using numerical methods to yield the values of the parameter sets $\theta_{RO}$ and $\theta_{CMB}$. If one or more individual parameters are known in advance, then their values can be fixed in equation (6). The dimension of the parameter space that is to be examined is reduced as a result. As an example, the elastic modulus E may be determined from prior experimentation and the value thus obtained may be fixed in equation (6). This would greatly reduce computational burden on the system.

Referring to FIG. 2, using the numerically determined values of the parameter set $\theta_{RO}$, the first curve 10 representing stress-strain characteristic may be fitted on the first set of data samples 11. Likewise, as shown in FIG. 3, using the numerically determined values of the parameter set $\theta_{CMB}$, the second curve 20 representing strain-life characteristic may be fitted on the second set of data samples 21.

As can be seen, the "curve fit" method proposed herein involves a problem of non-linear optimization that differs vastly from a conventional least squares (LS) fit method. Unlike in the conventional procedure with regard to the residues that are to be minimized, (i.e., amplitudes of stress and/or elastic and plastic strain), the dependent variables herein are identified as the stress amplitudes and the fatigue life span. This has proved to be extremely beneficial with regard to the robustness of the method, which is thus more reliable and obviates the need for providing high factors of safety in fatigue life estimation.

Referring back to FIG. 1, the design means 4 determines an estimated fatigue life of the component 6 on the basis of the LCF material curves obtained from the modeling means 3. Herein, based on calculated stresses in the component, resulting strains are calculated based on the stress-strain relationship given by first LCF material curve or RO curve as illustrated in FIG. 2. From these, LCF life times are obtained using the strain-life second LCF material curve or CMB curve as illustrated in FIG. 3.

The output of the design means 4 may comprise, for example, a prescribed number of cycles of operation for different levels of operational cyclic stress. Based on the output of the design means 4, the operation of the component 6 may be controlled by the control means 5. In particular, the control means 5 may be comprise prognosis means for scheduling and implementing appropriate downtimes or maintenance intervals for the component 6 taking into account the estimated life-span and operating stress on the component 6.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves, to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

The invention claimed is:

1. A method for fatigue life estimation of a component operable under cyclic stress, comprising:

obtaining, from strain controlled low cycle fatigue test data of the component or representative specimen of the component, a first set of data samples comprising measured stress amplitude values for varying test strain levels, and a second set of data samples comprising a plurality of measured cycles to crack initiation for varying test strain levels, and operating a processing device for:
fitting a first low cycle fatigue material curve on the first set of data samples and a second low cycle fatigue material curve on the second set of data samples, the first curve and the second curve are defined respectively by a first and a second set of curve parameters, wherein the values of the first and said second set of curve parameters are determined so as to maximize a likelihood function defined as $$L := \prod_{j=1}^{n} f_\sigma(\sigma_{a,j} \mid \theta_{C1}, \varepsilon_{a,j}) \cdot \prod_{k=1}^{m} f_N(N_{i,k} \mid \theta_{C2}, \varepsilon_{a,k}),$$

wherein
$f_\sigma$ and $f_N$ are probability distribution functions,
$\epsilon_{a,j}$ and $\epsilon_{a,k}$ represent test strain levels in the first and second sets of data samples respectively,
$\sigma_{a,j}$ represents measured stress amplitude values in the first set of data samples
$N_{i,k}$ represents the plurality of measured cycles to crack initiation in the second set of data samples,
$\theta_{C1}$ and $\theta_{C2}$ represent the first set and second set of curve parameters respectively; and
determining an estimated fatigue life of the component using the first and second low cycle fatigue material curves.

2. The method as claimed in claim 1, wherein determining the estimated fatigue life of the component by the processing device further comprises:
determining a resulting strain on the component using a first stress-strain relationship defined by the first low cycle fatigue material curve, the deteimining is based on a calculated stress in the component, and
determining a low cycle fatigue life of the component using a second strain-life relationship defined by the second LCF material curve, the determining is based on the determined resulting strain.

3. The method as claimed in claim 1, wherein the probability distribution functions $f_\sigma$ and $f_N$ represent log normal distributions.

4. The method as claimed in claim 1, wherein computing the first set and the second set of curve parameters comprises determining a plurality of parameters for which a negative logarithm of the likelihood functional assumes a minimum value, such that the likelihood functional is maximized.

5. The method as claimed in claim 1, wherein the first low cycle fatigue material curve is defined by a Romberg-Osgood equation based relationship between stress '$\sigma_a$' and strain '$\epsilon_a$', wherein $$\varepsilon_a = RO(\sigma_a) = \frac{\sigma_a}{E} + \left(\frac{\sigma_a}{K'}\right)^{1/n'},$$

and wherein E, K' and n' form the first set of curve parameters $\theta_{C1}$ the values of which are determined such that the likelihood function is maximized.

6. The method as claimed in claim 1, wherein the second low cycle fatigue material curve is defined by a Coffin-Manson-Basquin equation based relationship between strain '$\epsilon_a$' and a plurality of cycles to crack initiation '$N_i$', wherein $$\varepsilon_a = CMB(N_i) = \frac{\sigma'_f}{E}(2N_i)^b + \varepsilon'_f(2N_i)^c,$$

and wherein $\epsilon'_f$, $\sigma'_f$, E, b and c form the second set of curve parameters $\theta_{C2}$ the values of which are determined such that the likelihood function is maximized.

7. The method as claimed in claim 1, wherein a first parameter in the first set of parameters and a second parameter in the second set of parameters includes a predetermined fixed value from known material characteristics of the component.

8. A method for operating a component under cyclic stress, comprising:
controlling a downtime or maintenance interval of the component by taking into account an estimated fatigue life of the component,
wherein the estimated fatigue life is determined by the method of claim 1.

9. The method as claimed in claim 8, wherein the component is a gas turbine component.

10. A system for fatigue life estimation of a component under cyclic stress, comprising:
a testing means for performing a strain controlled low cycle fatigue test of the component or a representative specimen of the component, to obtain therefrom a first set of data samples comprising measured stress amplitude values for varying test strain levels, and a second set of data samples comprising a plurality of measured cycles to crack initiation for varying test strain levels,
a modeling means for fitting a first low cycle fatigue material curve on the first set of data samples and a second low cycle material curve on the second set of data samples, the first low cycle fatigue material curve and the second low cycle material are defined respectively by a first and a second set of curve parameters, wherein the values of the first and the second set of curve parameters are determined so as to maximize a likelihood functional defined as $$L := \prod_{j=1}^{n} f_\sigma(\sigma_{a,j} \mid \theta_{C1}, \varepsilon_{a,j}) \cdot \prod_{k=1}^{m} f_N(N_{i,k} \mid \theta_{C2}, \varepsilon_{a,k}),$$

wherein
$f_\sigma$ and $f_N$ are probability distribution functions,
$\epsilon_{a,j}$ and $\epsilon_{a,k}$ represent test strain levels in the first and second sets of data samples respectively,
$\sigma_{a,j}$ represents measured stress amplitude values in the first set of data samples
$N_{i,k}$ represents the measured number of cycles to crack initiation in the second set of data samples,
$\theta_{C1}$ and $\theta_{C2}$ represent the first set and second set of curve parameters respectively, and
a design means for determining an estimated fatigue life of the component using the first and second low cycle fatigue material curves.

11. The system as claimed in claim 10, wherein the design means is further adapted for determining an estimated fatigue life of the component by:
determining a resulting strain on the component based on a calculated stress in the component using a first stress-strain relationship defined by the first low cycle fatigue material curve, and
determining a low cycle fatigue life of the component based on the determined resulting strain using a second strain-life relationship defined by the second low cycle fatigue material curve.

12. The system as claimed in claim 10, further comprising a control means controlling a downtime or maintenance interval of the component by taking into account the estimated fatigue life of the component.

* * * * *